US011711065B2

(12) United States Patent
Broekaart et al.

(10) Patent No.: US 11,711,065 B2
(45) Date of Patent: *Jul. 25, 2023

(54) SUBSTRATE FOR A TEMPERATURE-COMPENSATED SURFACE ACOUSTIC WAVE DEVICE OR VOLUME ACOUSTIC WAVE DEVICE

(71) Applicant: Soitec, Bernin (FR)

(72) Inventors: Marcel Broekaart, Theys (FR); Thierry Barge, Chevrieres (FR); Pascal Guenard, Froges (FR); Ionut Radu, Crolles (FR); Eric Desbonnets, Lumbin (FR); Oleg Kononchuk, Theys (FR)

(73) Assignee: Soitec, Bernin (FR)

( * ) Notice: Subject to any disclaimer, the term of this patent is extended or adjusted under 35 U.S.C. 154(b) by 227 days.

This patent is subject to a terminal disclaimer.

(21) Appl. No.: 17/141,065

(22) Filed: Jan. 4, 2021

(65) Prior Publication Data

US 2021/0121103 A1 Apr. 29, 2021

Related U.S. Application Data

(63) Continuation of application No. 16/829,604, filed on Mar. 25, 2020, now Pat. No. 10,924,081, which is a (Continued)

(30) Foreign Application Priority Data

Dec. 22, 2015 (FR) ...................................... 1563058

(51) Int. Cl.
*A61B 5/1459* (2006.01)
*A61B 5/00* (2006.01)
(Continued)

(52) U.S. Cl.
CPC ....... *H03H 9/02834* (2013.01); *A61B 5/1459* (2013.01); *A61B 5/14546* (2013.01);
(Continued)

(58) Field of Classification Search
CPC ........ H03H 9/02834; H03H 3/02; H03H 3/04; H03H 3/10; H03H 9/02102;
(Continued)

(56) References Cited

U.S. PATENT DOCUMENTS

| | | |
|---|---|---|
| 4,019,200 A | 4/1977 | Adkins et al. |
| 6,700,631 B1 | 3/2004 | Inoue et al. |

(Continued)

FOREIGN PATENT DOCUMENTS

| | | |
|---|---|---|
| CN | 103718457 A | 5/2017 |
| EP | 2738939 A1 | 6/2014 |

(Continued)

OTHER PUBLICATIONS

European Search Report and Search Opinion Received for EP Application No. 21167505.3, dated Jul. 26, 2021, 6 pages.

(Continued)

*Primary Examiner* — Tong-Ho Kim
(74) *Attorney, Agent, or Firm* — TraskBritt

(57) ABSTRACT

A substrate for a surface acoustic wave device or bulk acoustic wave device, comprising a support substrate and an piezoelectric layer on the support substrate, wherein the support substrate comprises a semiconductor layer on a stiffening substrate having a coefficient of thermal expansion that is closer to the coefficient of thermal expansion of the material of the piezoelectric layer than that of silicon, the semiconductor layer being arranged between the piezoelectric layer and the stiffening substrate.

21 Claims, 4 Drawing Sheets

Related U.S. Application Data continuation of application No. 16/064,419, filed as application No. PCT/EP2016/082252 on Dec. 21, 2016, now Pat. No. 10,608,610.

(51) Int. Cl.

| | | |
|---|---|---|
| *A61B 5/145* | (2006.01) | |
| *H03H 9/02* | (2006.01) | |
| *H03H 3/02* | (2006.01) | |
| *H10N 30/072* | (2023.01) | |
| *H10N 30/87* | (2023.01) | |
| *H10N 39/00* | (2023.01) | |
| *H03H 3/04* | (2006.01) | |
| *H03H 3/10* | (2006.01) | |
| *H03H 9/13* | (2006.01) | |
| *H03H 9/145* | (2006.01) | |
| *H03H 9/17* | (2006.01) | |
| *H03H 9/25* | (2006.01) | |
| *H03H 9/56* | (2006.01) | |
| *H03H 9/64* | (2006.01) | |
| *H10N 30/085* | (2023.01) | |

(52) U.S. Cl.
CPC ............... *A61B 5/685* (2013.01); *H03H 3/02* (2013.01); *H03H 3/04* (2013.01); *H03H 3/10* (2013.01); *H03H 9/02102* (2013.01); *H03H 9/02574* (2013.01); *H03H 9/13* (2013.01); *H03H 9/145* (2013.01); *H03H 9/17* (2013.01); *H03H 9/25* (2013.01); *H03H 9/56* (2013.01); *H03H 9/6489* (2013.01); *H10N 30/072* (2023.02); *H10N 30/87* (2023.02); *H10N 39/00* (2023.02); *A61B 2562/0204* (2013.01); *H03H 2003/0407* (2013.01); *H10N 30/085* (2023.02)

(58) Field of Classification Search
CPC ...... H03H 9/02574; H03H 9/13; H03H 9/145; H03H 9/17; H03H 9/25; H03H 9/56; H03H 9/6489; H03H 2003/0407; A61B 5/14546; A61B 5/1459; A61B 5/685; A61B 2562/0204; H01L 27/20; H01L 41/047; H01L 41/312; H01L 41/335; H10N 30/072; H10N 30/87; H10N 39/00; H10N 30/085
USPC ......................................................... 257/416
See application file for complete search history.

(56) References Cited

U.S. PATENT DOCUMENTS

| | | | |
|---|---|---|---|
| 10,608,610 B2* | 3/2020 | Broekaart | H03H 9/02834 |
| 2003/0008437 A1 | 1/2003 | Inoue et al. | |
| 2004/0241902 A1 | 12/2004 | Letertre et al. | |
| 2014/0130319 A1* | 5/2014 | Iwamoto | H03H 3/02 29/25.35 |
| 2014/0139075 A1* | 5/2014 | Iwamoto | H03H 3/10 29/25.35 |
| 2015/0102705 A1 | 4/2015 | Iwamoto et al. | |
| 2019/0007024 A1 | 1/2019 | Broekaart et al. | |

FOREIGN PATENT DOCUMENTS

| | | |
|---|---|---|
| FR | 2816445 A1 | 5/2002 |
| JP | 08-153915 A | 6/1996 |
| JP | 11-312811 A | 11/1999 |
| JP | 2006-005433 A | 1/2006 |
| JP | 2007-503726 A | 2/2007 |
| JP | 2010-153962 A | 7/2010 |
| JP | 2015-073331 A | 4/2015 |
| WO | 2004/109781 A1 | 12/2004 |
| WO | 2011/074329 A1 | 6/2011 |
| WO | 2013/018604 A1 | 2/2013 |

OTHER PUBLICATIONS

European Search Report and Written Opinion from European Application No. 21167505.3, dated Jul. 15, 2021, 8 pages.
Japanese Decision to Grant for Japanese Application No. 2018-532612 dated Feb. 2, 2021, 5 pages with English Translation.
Chinese First Office Action for Application No. 201680079260.X dated Apr. 6, 2021, 10 pages.
French Search Report and Written Opinion from French Application No. 1563058, dated Aug. 18, 2016, 6 Pages.
Japanese Office Action for Japanese Application No. 2018532612, dated Nov. 13, 2020, for JP Application No. 2018-532612, 8 pages including English translation.
Singapore Written Opinion from Singapore Application No. 11201805398V, dated May 13, 2020, 5 pages.
Hashimoto et al., Recent Development of Temperature Compensated SAW Devices, Ultrasonics Symposium (IUS), Oct. 18-21, 2011, pp. 79-86.
International Search Report for International Application No. PCT/EP2016/082252 dated Mar. 23, 2017, 2 pages.
International Written Opinion for International Application No. PCT/EP2016/082252 dated Mar. 23, 2017, 5 pages.
Japanese Office Action for JP Application No. 2018-532612 dated Sep. 4, 2020, 8 pages with English Translation.
Singapore Written Opinion for SG Application No. 11201805398V dated Jun. 4, 2019, 6 pages.

\* cited by examiner

SUBSTRATE FOR A TEMPERATURE-COMPENSATED SURFACE ACOUSTIC WAVE DEVICE OR VOLUME ACOUSTIC WAVE DEVICE

CROSS-REFERENCE TO RELATED APPLICATIONS

This application is a continuation of U.S. patent application Ser. No. 16/829,604, filed Mar. 25, 2020, now U.S. Pat. No. 10,924,081, issued Feb. 16, 2021, which is a continuation of U.S. patent application Ser. No. 16/064,419, filed Jun. 20, 2018, now U.S. Pat. No. 10,608,610, issued Mar. 31, 2020, which is a national phase entry under 35 U.S.C. § 371 of International Patent Application PCT/EP2016/082252, filed Dec. 21, 2016, designating the United States of America and published as International Patent Publication WO 2017/109000 A1 on Jun. 29, 2017, which claims the benefit under Article 8 of the Patent Cooperation Treaty to French Patent Application Serial No. 1563058, filed Dec. 22, 2015, the disclosure of each of which is hereby incorporated herein in its entirety by this reference.

TECHNICAL FIELD

This application relates to a substrate for a temperature-compensated surface acoustic wave device or a bulk acoustic wave device as well as a method for manufacture of such a substrate and a surface acoustic wave device or bulk acoustic wave device comprising such a substrate.

BACKGROUND

Surface Acoustic Wave devices, generally designated by the acronym SAW devices, find applications in the field of radio-frequency (RF) communications and, in particular, for filter applications.

A SAW device typically comprises a piezoelectric layer and two electrodes in the form of two interdigitated metallic combs deposited on the surface of the piezoelectric layer.

An electrical signal, such as an electrical voltage change applied to an electrode, is converted into an elastic wave, which is propagated at the surface of the piezoelectric layer. The wave is converted once more into an electrical signal on reaching the other electrode.

The choice of the piezoelectric material takes into account the electromagnetic coupling coefficient, which expresses the rate of electromagnetic conversion by the material, and the temperature stability of the oscillation frequency of the piezoelectric material.

SAW devices are very sensitive to variations in temperature, which induce different degrees of expansion of the piezoelectric layer and of the metallic electrodes due to the different coefficients of thermal expansion of these materials.

More precisely, the Temperature Coefficient of Frequency referred to by the acronym TDF and defined as the variation of a given frequency f as a function of the temperature T, is given by the formula:

$$TCF = \frac{1}{f}\frac{\partial f}{\partial T} = TCV - CTE$$

where:

$$TCV = \frac{1}{V}\frac{\partial V}{\partial T}$$

V is the speed of the surface acoustic waves and CTE is the coefficient of thermal expansion of the piezoelectric material in the direction of propagation of the surface acoustic waves.

Measures already exist for compensating for the effects of temperature on SAW devices.

In particular, the article by Hashimoto et al. [1] provides a review of the various temperature-compensation techniques for SAW devices.

Amongst these different techniques, the following can essentially be distinguished:

(1) a so-called "overlay" technique consisting of covering the surface of the piezoelectric layer and the electrodes with a dielectric material (typically silicon oxide ($SiO_2$)), which exhibits a coefficient of thermal expansion in the opposite sense to that of the piezoelectric layer, (2) a so-called "wafer-bonding" technique consisting of bonding the piezoelectric layer to a support substance whose coefficient of thermal expansion is as low as possible so as to neutralize the thermal expansion of the piezoelectric layer.

The support substrate, which may be made, for example, of silicon, of sapphire, of glass or of spinel ($MgAl_2O_4$), thus performs a stiffening function of the piezoelectric layer. Given its thickness, the piezoelectric layer is considered to extend to infinity in a direction away from the electrodes, so that the presence of the support substrate does not interfere with the propagation of the surface acoustic waves. Nevertheless, the bonding of the support substrate appears to create spurious resonances at frequencies greater than the principal frequency of the device (see [1], FIG. 5).

Of the materials envisaged for the support substrate in this second technique, silicon seems to be the most promising as it allows integration methods for electronic components at the substrate scale (so-called "wafer level") to be implemented.

Nevertheless, a significant difference in thermal expansion coefficients exists between the piezoelectric material and silicon (for a crystal of $LiTaO_3$, which is anisotropic, the CTE values are about $4 \times 10^{-6}/°C$ and $14 \times 10^{-6}/°C$, while the CTE of silicon is of the order of $2.3 \times 10^{-6}/°C$), which affects the stability of the support substrate/piezoelectric layer stack if the latter is exposed to high temperatures during the subsequent steps in the method for manufacture of the surface acoustic wave device. In light of such steps, thermal stability of the piezoelectric layer/support substrate stack must be ensured up to a temperature of about 250° C.

A similar problem arises for bulk (volume) acoustic wave filters and resonators, known by the acronym BAW.

Bulk acoustic wave filters and resonators typically comprise a thin piezoelectric layer (that is, with a thickness in general of less than 1 µm) and two electrodes arranged on each principal face of the thin layer. An electrical signal, such as an electrical voltage change applied to an electrode, is converted into an elastic wave, which is propagated through the piezoelectric layer. This wave is converted once more into an electrical signal on reaching the electrode located on the opposite face.

BRIEF SUMMARY

One aim of the disclosure is to design a substrate for a temperature-compensation surface wave acoustic device or bulk acoustic wave device that overcomes the above-mentioned drawbacks. In particular, such a substrate must be more stable than the above-mentioned silicon support substrate/piezoelectric layer stack up to a temperature of about 300° C., while allowing easy integration of electronic components.

In accordance with the disclosure, a substrate is proposed for a surface acoustic wave device or bulk acoustic wave device that comprises a support substrate and a piezoelectric layer on the support substrate, wherein the support substrate comprises a semiconductor layer on a stiffening substrate that has a coefficient of thermal expansion closer to the coefficient of thermal expansion of the material of the piezoelectric layer than that of silicon, where the semiconductor layer is arranged between the piezoelectric layer and the stiffening substrate.

The stiffening substrate advantageously comprises sapphire, glass and/or spinel ($MgAl_2O_4$).

The semiconductor layer is preferably formed from one of the following materials: silicon, germanium, SiGe, SiC, a III-V material.

Particularly advantageously, the semiconductor layer comprises at least one electronic component. The electronic component may, in particular, be chosen from amongst a CMOS transistor, a switch and a power amplifier.

According to one embodiment, the ratio of the thickness of the piezoelectric layer to the thickness of the stiffening substrate is less than or equal to 0.125.

For example, the thickness of the piezoelectric layer is less than 50 μm, preferably less than 20 μm, yet more preferably less than 1 μm and the thickness of the stiffener substrate is between 400 and 800 μm.

According to one embodiment, the substrate comprises a dielectric layer between the piezoelectric layer and the semiconductor layer and a charge-trapping layer at the interface between the dielectric layer and the semiconductor layer and/or the interface between the dielectric layer and the piezoelectric layer.

The charge-trapping layer may comprise a polycrystalline silicon layer.

In the case of the piezoelectric layer being anisotropic and, therefore, exhibiting at least two different coefficients of thermal expansion in a plane parallel to a principal face of the substrate, the coefficient of thermal expansion, which results in the greatest discrepancy in relation to the coefficient of thermal expansion of the stiffening substrate, is considered.

The disclosure also relates to a surface acoustic wave device comprising a substrate as described above and two electrodes formed of two interdigitated metallic combs on the surface of the piezoelectric layer.

The disclosure also relates to a bulk acoustic wave device comprising a substrate as described above and two electrodes arranged on either side of the piezoelectric layer.

Another object relates to a method of manufacture of a substrate as described above, wherein the method comprises:
 the transfer of the semiconductor layer onto the stiffening substrate from a first donor substrate,
 the transfer of the piezoelectric layer onto the semiconductor layer from a second donor substrate.

According to one embodiment, at least one of the transfer steps comprises the following sub-steps:
 formation of an embrittlement zone in the first and second donor substrates, respectively, by the implantation of atomic species;
 bonding of the first and second donor substrates, respectively, onto the stiffener substrate and semiconductor layer, respectively;
 detachment of the first and second substrates, respectively, along the embrittlement zone.

BRIEF DESCRIPTION OF DRAWINGS

Other characteristics and advantages of the disclosure will emerge from the detailed description that follows, with reference to the accompanying drawings, in which.

For readability purposes, the elements shown are not necessarily shown to scale. In addition, the same components are designated by the same reference symbols on the various figures.

DETAILED DESCRIPTION

Figure 1:
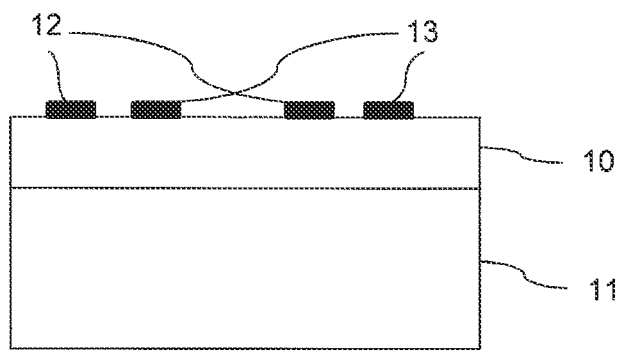
FIG. 1 is a schematic cross-sectional view of a temperature-compensated surface acoustic wave filter.

FIG. 1 is a schematic view of a surface acoustic wave filter.

The filter comprises a piezoelectric layer 10 and two electrodes 12, 13 in the form of two interdigitated metallic combs deposited on the surface of the piezoelectric layer. On the side away from the electrode 12, 13, the piezoelectric layer rests on a support substrate 11 intended to provide temperature compensation and whose structure will be described in detail below. The piezoelectric layer 10 preferably has excellent crystalline quality in order not to cause attenuation of the surface wave. The layer is, therefore, monocrystalline. Currently, suitable materials that can be used industrially are quartz, $LiNbO_3$ or $LiTaO_3$. The piezoelectric layer 10 is generally obtained by sectioning an ingot of one of the materials, where the required precision for the thickness of the layer is not great insofar as the waves must essentially be propagated at its surface.

Figure 2:
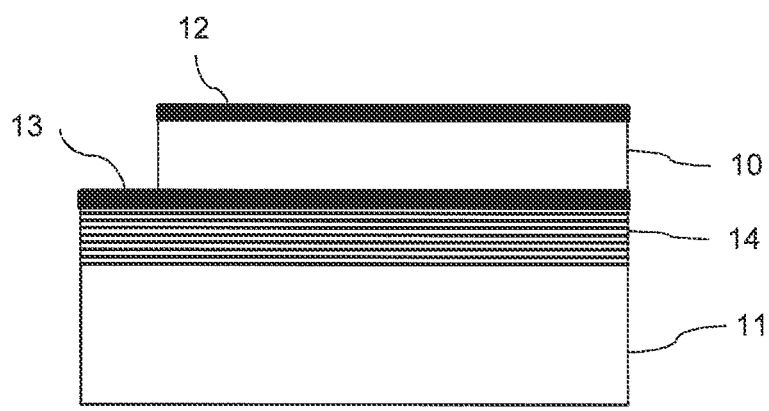
FIG. 2 is a schematic cross-sectional view of a temperature-compensated bulk acoustic wave resonator.

FIG. 2 is a schematic view of a bulk acoustic wave resonator.

The resonator comprises a thin piezoelectric layer (that is, with a thickness in general of less than 20 nm) and two electrodes 12, 13 arranged on either side of the piezoelectric layer 10. The piezoelectric layer 10 rests on a support substrate 11 whose structure will be described in detail below. To isolate the resonator from the substrate and thus avoid propagation of waves into the substrate, a Bragg mirror 14 is interposed between the electrode 13 and the support substrate 11. Alternatively (not shown), isolation could be achieved by arranging a cavity between the substrate and the piezoelectric layer. These various arrangements are known to those skilled in the art and are, therefore, not described in detail in the present description.

For a bulk acoustic wave device, the piezoelectric layer 10 has a determined uniform thickness over the entire layer. On the other hand, since crystalline quality does not rely on any particular importance in terms of resonator performance, a polycrystalline piezoelectric material is acceptable. The piezoelectric layer 10 is, therefore, in general, formed by deposition onto a support (for example, a silicon support). The materials currently used industrially for such deposition are AlN, ZnO and PZT.

Figure 3:
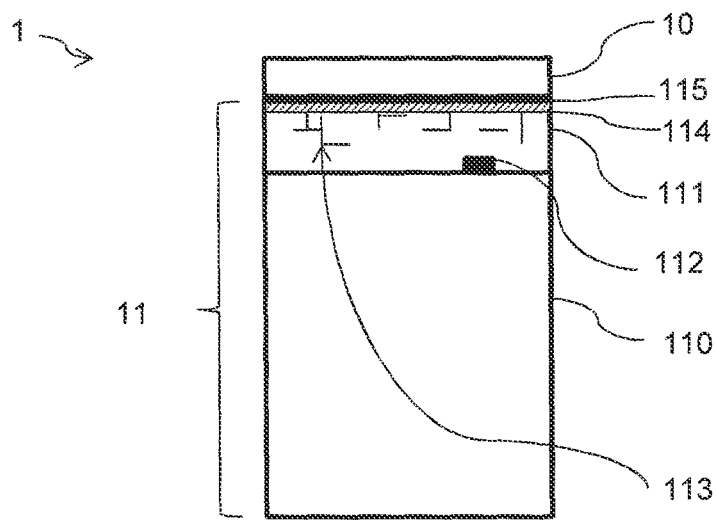
FIG. 3 is schematic cross-sectional view of a substrate according to one embodiment form of the disclosure.

FIG. 3 is a schematic cross-sectional view of a substrate used to manufacture a temperature-compensated surface acoustic wave device or bulk acoustic wave device according to one embodiment form of the disclosure.

Substrate 1 comprises a piezoelectric layer 10 intended to receive electrodes in order to form a surface acoustic wave device or bulk acoustic wave device.

The material, the crystalline quality and the thickness of the piezoelectric layer 10 are selected by those skilled in the art depending on the target application. Selection criteria are themselves known and do not need to be described in detail in the present description.

If the selected piezoelectric material is anisotropic, the latter has different coefficients of thermal expansion in different directions.

The piezoelectric layer 10 is arranged on a composite support substrate 11, that is, one formed from a stack of several layers of different materials.

The support substrate 11 comprises a so-called stiffening substrate 110, whose function within the substrate 1 is to ensure the rigidity of the stack, in particular, during heat treatment operations.

The stiffening substrate 110 advantageously comprises sapphire, glass and/or spinel ($MgAl_2O_4$).

These materials have the advantage of offering a coefficient of thermal expansion closer to the coefficient of thermal expansion of the piezoelectric material than silicon, providing improved temperature stability (up to about 300° C.) of the stack, although this increased closeness of the coefficient of thermal expansion is slightly detrimental to the temperature-compensation effect.

The stiffening substrate 110 moreover exhibits a large thickness, typically of the order of 400 to 800 μm, which is much greater than the thickness of the other layers of the substrate 1 and, in particular, much greater than the thickness of the piezoelectric layer, which is in general less than 50 μm, preferably less than 20 μm and yet more preferably less than 1 μm. Thus, the temperature behavior of the stiffening substrate predominates compared with that of the other layers.

Due to the relative closeness of the coefficients of thermal expansion of the stiffening substrate 110 and of the piezoelectric layer 10, the stresses due to the difference in coefficients of thermal expansion during the heat treatment that the substrate 1 undergoes are minimized.

A semiconductor layer 111 is inserted between the stiffening substrate 110 and the piezoelectric layer 10. The semiconductor layer may comprise silicon, germanium, SiGe, SiC, or a III-V type material such as GaAs, GaN or InGaN (this list is non-restrictive). Of these materials, germanium and GaAs are less preferable because of their fragility. According to one preferred embodiment form of the disclosure, the semiconductor layer is a layer of silicon.

Particularly advantageously, the semiconductor layer 111 comprises at least one electronic component 112. The component is manufactured using techniques known in microelectronics. This may be a CMOS transistor, a switch, or a power amplifier (this list is not restrictive). Moreover, pathways 113 may be made on the interior of the semiconductor layer 111 so as to allow electrical connection of various components. These components and pathways are formed by conventional microelectronic techniques, which are not described in detail in the present description.

The semiconductor layer 111 is substantially thinner than the stiffening substrate 110. Thus, the semiconductor layer 111 typically has a thickness of between 10 nm and 2 μm. Consequently, even if the material of the semiconductor layer has a difference in coefficient of thermal expansion relative to the piezoelectric material that is greater than the difference in coefficient of thermal expansion between the material of the stiffening substrate 110 and the piezoelectric layer 10, the semiconductor layer 111 is thin enough not to generate mechanical stress in the piezoelectric layer 10 during heat treatment.

Moreover, in comparison with a bulk sapphire substrate, the composite support substrate 11 formed of the sapphire stiffening substrate 110 and of the semiconductor layer 111 allow electronic components to be integrated into the rear face of the piezoelectric layer 10.

According to one advantageous but not mandatory embodiment form, a dielectric layer 114 is arranged at the interface between the semiconductor layer 111 and the piezoelectric layer 10. Such a dielectric layer is, in general, used to promote the bonding of the piezoelectric layer 10 onto the semiconductor layer 111. The dielectric layer may be formed, prior to the bonding of the piezoelectric layer 10 on the semiconductor layer 111, either on only one of these layers, or on each of them (oxide-oxide type bonding being performed in the latter case). In this event, a charge-trapping layer 115 is made beneath the piezoelectric layer, advantageously interposed between the dielectric layer 114 and the piezoelectric layer 10, or between the semiconductor layer 111 and the dielectric layer 114 in order to trap electric charge present, which could interfere with the operation of electronic components arranged within the semiconductor layer 111. The charge-trapping layer 115 may comprise, for example, a layer of polycrystalline or amorphous silicon. Any other layer (or stack of layers) that fulfills the electric charge-trapping function may be used, however.

Figure 4:
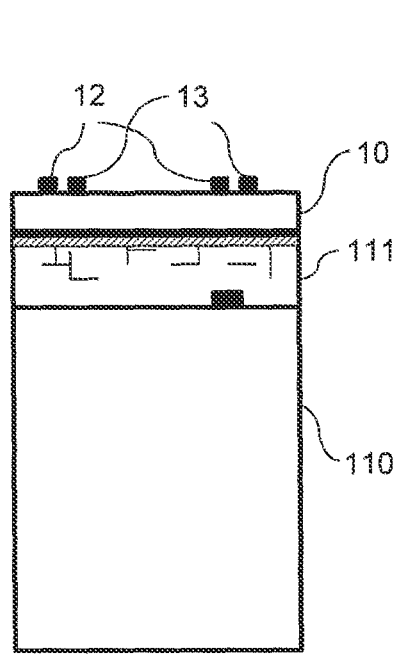
FIG. 4 is a schematic cross-sectional view of a temperature-compensated surface acoustic wave filter according to one embodiment of the disclosure.

FIG. 4 schematically shows a surface acoustic wave filter formed on the substrate 1 of FIG. 3. To this end, metallic electrodes 12, 13 have been deposited in the form of two interdigitated combs on the free surface of the piezoelectric layer 10.

Figure 5:
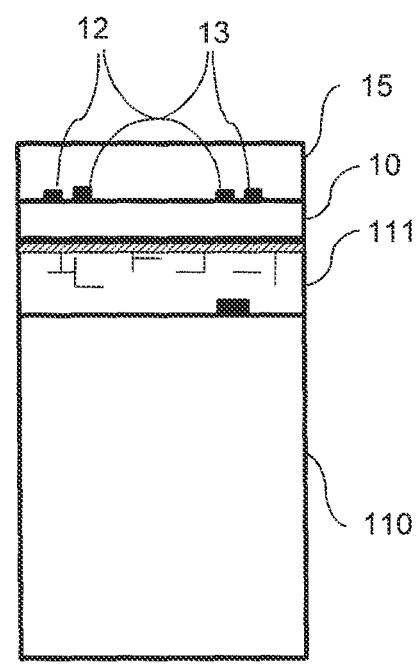
FIG. 5 is a schematic cross-sectional view of a temperature-compensated surface acoustic wave filter according to an alternative embodiment of the disclosure.

According to one alternative embodiment shown in FIG. 5, the substrate may, after electrodes 12, 13 are formed on the piezoelectric layer 10, be covered with a layer of dielectric (typically silicon oxide ($SiO_2$)) in accordance with the "overlay" technique mentioned above. The thickness of the dielectric layer 15 is typically of the order of 100 to 10,000 nm.

Compared with the embodiment in FIG. 4, the dielectric layer 15, which has a coefficient of thermal expansion, which is in the opposite sense to that of the piezoelectric layer 10, provides improved temperature compensation.

A method of manufacture of a substrate for a surface acoustic wave device or bulk acoustic wave device according to one non-restrictive embodiment of the disclosure will now be described with reference to FIGS. 6A to 6E. The method described below involves bonding then thinning of a donor substrate, but other techniques such as a "removable substrate" type as described in document FR 2 816 445 may be employed. Such a "removable" substrate is made before the manufacture of components and contains an embrittlement zone or interface, which allows the donor substrate to be broken after assembly on a stiffening substrate.

Figure 6A:
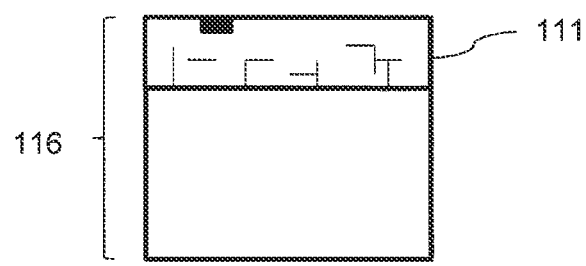
FIGS. 6A to 6E show successive steps in the manufacture of a substrate according to one embodiment of the disclosure.

With reference to FIG. 6A, a donor substrate 116 is provided, which comprises the semiconductor layer 111 wherein electronic components 112 and/or pathways 113 are advantageously incorporated, in accordance with techniques widely used in microelectronics.

Figure 6B:
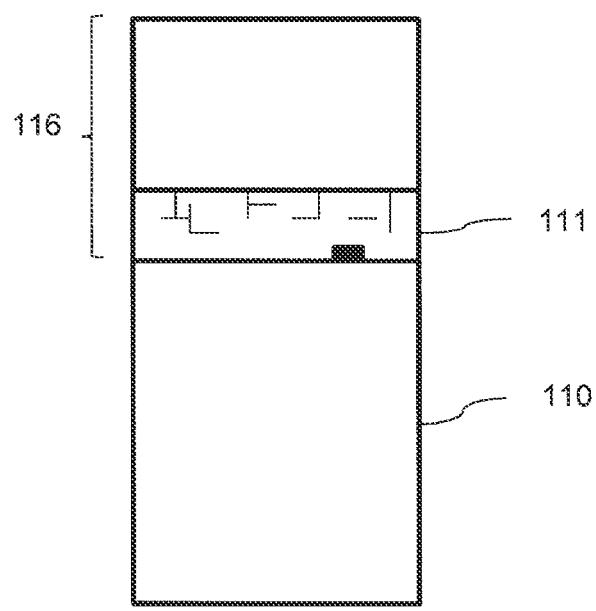

With reference to FIG. 6B, the donor substrate 116 is bonded onto the stiffening substrate 110, so that the semiconductor layer 111 is located at the bonding interface.

Figure 6C:
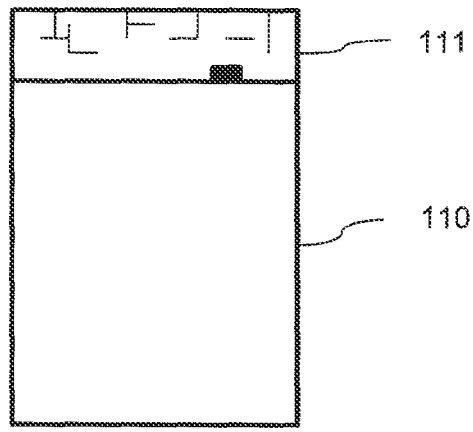

With reference to FIG. 6C, the donor substrate is made thinner through the side away from the semiconductor layer 111 so as to transfer the layer comprising the semiconductor layer 111 onto the stiffening substrate 110. Thinning may be mechanical (of the polishing type), chemical (etching) or other. If necessary, the electronic components and/or pathways are then integrated in the layer.

Figure 6D:
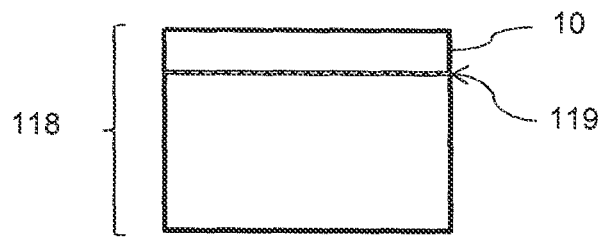

With reference to FIG. 6D, a piezoelectric donor substrate 118 is provided made of a piezoelectric material and an embrittlement zone 119 is formed, by implantation of atomic species in the substrate, which demarcates a piezoelectric layer to be transferred, namely the piezoelectric layer 10 of the final substrate shown in FIG. 3. The implantation conditions are known in the state of the art, namely, a dose of the order of 5 to 15E16 and energy of between 20 and 200 keV.

Figure 6E:
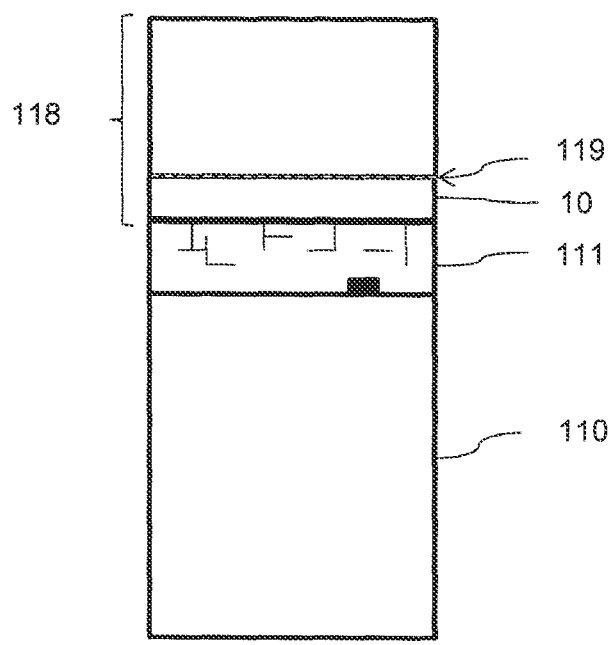

With reference to FIG. 6E, the piezoelectric donor substrate 118 is bonded onto the stack formed from the stiffening substrate 110 and the semiconductor layer 111, so that the semiconductor layer 111 and the piezoelectric layer 10 are at the bonding interface. As stated above, a dielectric layer (not shown in FIG. 6E) can be formed beforehand on one and/or the other of these layers in order to promote bonding. If necessary, a charge-trapping layer (not shown in FIG. 6E) may be formed between the dielectric layer and the piezoelectric layer. The trapping layer is advantageously formed after implantation performed in the piezoelectric donor substrate 118. Under these conditions, a low-temperature method is required. For example, a layer of amorphous silicon is deposited on the piezoelectric substrate or a layer of polycrystalline silicon is deposited on a dielectric layer formed on the semiconductor layer 111.

In cases where it is wished to form a bulk acoustic wave device, the bonding may be achieved by means of a metallic layer, the layer then fulfilling the role of an electrode buried in the device.

The piezoelectric donor substrate 118 is split along the embrittlement zone 119 so as to transfer the piezoelectric layer 10 onto the semiconductor layer 111. Thinning of the piezoelectric layer may be implemented if necessary in order to remove defects associated with the implantation.

In the case where the semiconductor layer does not comprise electronic components, the SMART CUT® method can also be implemented in order to transfer the semiconductor layer 111 onto the stiffening substrate 110. This process is well known to those skilled in the art. In particular, an embrittlement zone is formed by implantation of atomic species in the donor substrate 116, so as to demarcate a layer to be transferred that comprises the semiconductor layer 111. This implantation also uses hydrogen and/or helium atoms, and those skilled in the art are able to determine the implantation dose and energy depending on the donor substrate material and the depth to be reached. Then, after bonding of the donor substrate onto the stiffening substrate 110, the donor substrate is detached along the embrittlement zone; this detachment may be initiated mechanically, chemically or by other means.

In the event that it is wished to manufacture a surface acoustic wave device, metallic electrodes in the form of two interdigitated combs are then deposited on the surface of the piezoelectric layer 10.

In the event that it is wished to manufacture a bulk acoustic wave device, the steps described above must be adapted. On the one hand, before the bonding step shown in FIG. 6E, a first electrode is deposited on the free surface of the piezoelectric layer 10 forming part of the piezoelectric donor layer, where this first electrode is located buried in the final stack. After the transfer of the piezoelectric layer 10 onto the semiconductor layer 111, a second electrode is deposited onto the free surface of the piezoelectric layer that is away from the first electrode. On the other hand, in order to prevent propagation of acoustic waves in the semiconductor layer 111 and in the stiffening substrate 110, a means of isolation may be incorporated into the semiconductor layer 111, where the means of isolation can be, for example, a Bragg mirror 14 (as shown in FIG. 2) or a cavity etched into the semiconductor layer 111.

REFERENCES

[1] Hashimoto et al., Recent Development of Temperature Compensated SAW Devices, Ultrasonics Symposium (IUS), 18-21 Oct. 2011, pp. 79-86, 2011 IEEE International

FR 2 816 445

What is claimed is:

1. A bulk acoustic wave device, comprising:
a stiffening substrate;
a piezoelectric layer disposed over the stiffening substrate;
a semiconductor layer disposed between the piezoelectric layer and the stiffening substrate; and
a first electrode disposed on a surface of the piezoelectric layer on a side of the piezoelectric layer opposite the stiffening substrate, and a second electrode disposed between the piezoelectric layer and the stiffening substrate, the first electrode and the second electrode configured to generate or receive acoustic waves within the piezoelectric layer.

2. The bulk acoustic wave device of claim 1, further comprising a dielectric layer between the piezoelectric layer and the semiconductor layer.

3. The bulk acoustic wave device of claim 2, wherein the dielectric layer comprises silicon oxide.

4. The bulk acoustic wave device of claim 1, further comprising a charge-trapping layer between the piezoelectric layer and the stiffening substrate.

5. The bulk acoustic wave device of claim 4, wherein the charge-trapping layer comprises polycrystalline silicon.

6. The bulk acoustic wave device of claim 1, wherein the piezoelectric layer is monocrystalline.

7. The bulk acoustic wave device of claim 1, wherein the piezoelectric layer comprises a material selected from the group consisting of: lithium niobate ($LiNbO_3$), lithium tantalate ($LiTaO_3$), and quartz.

8. The bulk acoustic wave device of claim 1, wherein a thickness of the piezoelectric layer is less than 50 µm, and a thickness of the stiffening substrate is between 400 and 800 µm.

9. The bulk acoustic wave device of claim 8, wherein the thickness of the piezoelectric layer is less than 20 µm.

10. The bulk acoustic wave device of claim 9, wherein the thickness of the piezoelectric layer is less than 1 µm.

11. The bulk acoustic wave device of claim 1, wherein a thickness of the semiconductor layer is between 10 nm and 2 µm.

12. The bulk acoustic wave device of claim 1, wherein the semiconductor layer comprises a material selected from the group consisting of: silicon, germanium, SiGe, SiC, and a III-V material.

13. The bulk acoustic wave device of claim 1, wherein the semiconductor layer comprises at least one electronic component.

14. The bulk acoustic wave device of claim 13, wherein the at least one electronic component comprises a component selected from the group consisting of: a CMOS transistor, a switch, and a power amplifier.

15. The bulk acoustic wave device of claim 1, wherein the stiffening substrate comprises sapphire, glass and/or spinel (MgAl$_2$O$_4$).

16. The bulk acoustic wave device of claim 1, wherein a ratio of a thickness of the piezoelectric layer to a thickness of the stiffening substrate is less than or equal to 0.125.

17. A bulk acoustic wave device, comprising:
a stiffening substrate;
a piezoelectric layer;
a semiconductor layer disposed between the piezoelectric layer and the stiffening substrate; and
electrodes disposed on opposing sides of the piezoelectric layer, the electrodes configured to generate or receive bulk acoustic waves in the piezoelectric layer.

18. A method of manufacturing a bulk acoustic wave device, comprising:
transferring a semiconductor layer from a first donor substrate onto a stiffening substrate to form a support substrate;
transferring a piezoelectric layer onto the support substrate from a second donor substrate such that the semiconductor layer is disposed between the piezoelectric layer and the stiffening substrate; and
providing electrodes disposed on opposing sides of the piezoelectric layer, the electrodes configured to generate or receive bulk acoustic waves in the piezoelectric layer.

19. The method of claim 18, further comprising forming a charge-trapping layer between the piezoelectric layer and the stiffening substrate.

20. The method of claim 18, wherein at least one of transferring the semiconductor layer and transferring the piezoelectric layer comprises:
forming an embrittlement zone in the first or second donor substrate, respectively, by implantation of atomic species;
bonding the first or second donor substrate, respectively, onto the stiffening substrate or semiconductor layer, respectively; and
detaching the first or second donor substrate, respectively, along the embrittlement zone.

21. The method of claim 20, wherein the bonding of the first or second donor substrate, respectively, onto the stiffening substrate or semiconductor layer, respectively, comprises:
depositing a first metal layer on the first or second donor substrate;
depositing a second metal layer on the stiffening substrate or semiconductor layer; and
bonding the first metal layer to the second metal layer, the bonded first metal layer and the second metal layer forming one electrode of the electrodes disposed on opposing sides of the piezoelectric layer.

* * * * *